US00PP11892P2

(12) United States Plant Patent
Kent

(10) Patent No.: US PP11,892 P2
(45) Date of Patent: May 29, 2001

(54) GUZMANIA PLANT NAMED 'GUZ 224'

(75) Inventor: Jeffrey C. Kent, 2074 Pleasant Heights, Vista, CA (US) 92084

(73) Assignee: Jeffrey C. Kent, Vista, CA (US)

( * ) Notice: Subject to any disclaimer, the term of this patent is extended or adjusted under 35 U.S.C. 154(b) by 0 days.

(21) Appl. No.: 09/247,341

(22) Filed: Feb. 9, 1999

(51) Int. Cl.[7] ..... A01H 5/00
(52) U.S. Cl. ..... Plt./371
(58) Field of Search ..... Plt./371

(56) References Cited

U.S. PATENT DOCUMENTS

P.P. 9,476 * 3/1996 Kent ..... Plt./371

* cited by examiner

*Primary Examiner*—Bruce R. Campell
*Assistant Examiner*—Kent L. Bell
(74) *Attorney, Agent, or Firm*—James A. Lucas; Driggs, Lucas, Brubaker & Hogg Co. L.P.A.

(57) ABSTRACT

A new cultivar of Guzmania named 'GUZ 224 ' characterized by having rich red-purple floral bracts, longitudinally variegated leaves and a compact arrangement of scape and floral bracts.

1 Drawing Sheet

BACKGROUND OF THE INVENTION

The present invention relates to a newly developed interspecific hybrid Guzmania plant resulting from a planned breeding program that I conduct on an ongoing basis. The objects of the breeding program include the crossing of selected parent plants from the numerous, compatible species within the genus, to obtain plants with novel and attractive phenootypes, coloration, and flowering forms. Other important selection factors may include ultimate plant size and shape, disease resistance, tolerance to different soil and growing conditions and vigor.

Among the objects of my program are to produce plants of the Bromeliaceae family which will be attractive to the consumer, which will develop reasonably rapidly under controlled conditions; and which retain for a long term, highly attractive and bright inflorescences; i.e., bract coloration, after being induced into the flowering stage. It is a specific object to provide a low maintenance plant which will be a long term decorative appointment offering an exotic color splash in the home of a buyer, or to serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The plant of this disclosure was a naturally occurring vegetative sport discovered as a single plant growing in a cultivated planting of the parent Guzmania 'Irene', an unpatented $F_1$ hybrid of *Guzmania lingulata* 'Panama Red'× *Guzmania wittmackii* 'Lila'. With the recognition that this sport satisfied the objects of the breeding program, the individual was isolated and set aside for further observation and testing. The resulting selection has been assigned the designation 'GUZ 224' for purposes of identification. This plant has been reproduced by division at Vista Calif., and the clonal specimens resulting therefrom have been determined to be identical to the original selection in all distinguishing characteristics. The superior attributes of this plant will be revealed in the botanical descriptions to follow.

SUMMARY OF THE INVENTION

The following attributes of the plant 'GUZ 224' distinguish it from other clones of 'Irene'. The foliage of 'GUZ 224' is strikingly different than that of 'Irene' which has broad leaves RHS147-A in color. The leaves of 'GUZ 224' are variegated longitudinally but not on margins; The variegation is 149-D in color suffusing into white coloration from approximately the middle to the apex; The variegated portion occupies ⅔ of the leaf surface; This leaf coloration gives this plant a contrasting foliage and brightens the appearance of the floral spikes. The plant mutation has rich red and purple floral bracts and variegated leaves. It grows somewhat slower than other variegated mutations, taking about 20 weeks in the summer and about 22 weeks in the winter in USDA hardiness zone 9 to grow from offset to marketable size. The bracts are more compact and closer together giving a more compact effect than other clones. The colors in the bracts remain vivid indoors for at least 8 weeks.

BRIEF DESCRIPTION OF THE DRAWING

The single color photograph depicts a mature specimen of the plant in mid to late flowering stage. Illustrated are the mature leaves, scape bracts and floral bracts. The color definitions in the specification have been taken from The R.H.S. Colour Chart of the Royal Horticultural Society. While the colors depicted are believed to be of a high level of color fidelity, the coloration of this plant should be understood to be approximate, and somewhat variable as a function of cultural conditions and horticultural practices. For example, the bract color might slightly fade if the plants is subjected to bright light and the leaf color may vary depending on the composition and the concentration of fertilizer that may be applied to the plant.

BOTANICAL DESCRIPTION OF THE PLANT

General characteristics:

*Type.*—Type-Monocot perennial.

*Habit.*—vigorous, upright, spreading and open. The plant grows from initial transplant to anthesis in 15 months in coastal southern California.

*Hardiness.*—Tender. Leaves are damaged at temperatures below 32° F.; Buds are destroyed at temperatures below 32° F.; Entire plant will not survive exposure to temperatures below 32° F. for several hours.

*Size.*—Large, about 43–45 inches in width and about 25–27 inches in height, including inflorescence.

*Shape.*—Vase formed.

Leaves:

*Length.*—22–24 inches.

*Width.*—2 inches.

*Medium.*—Large in size, slightly acuminate at tips, light green, linear, medium thickness, smooth with smooth margins, apetiolate. Leaves arching, somewhat truncate at the base, margins 1/32–3/4 inch broad; 143-C in color adaxial and abaxial; variegatated longitudinally, but not on the margins, 149-D in color suffusing into white coloration from approximately the middle to the apex; lower leaves stained and blotched 167-C in color on adaxial and abaxial, but appearing more on the abaxial. This coloring takes over more of the leaf upwards to the scape bracts.

Scape bracts: Nearly 90° to the scape somewhat drooping particularly at the tips, tips acuminate and acutely pointed 7 7/8×1 3/8 to 3 1/4×1 1/4 inches at the apex. Color of bracts are solid 67-C except for the unvariegated portions which are 79-A in color on the lower bracts and 71-A on the upper bracts, adaxial and abaxial. Lower bracts are 150-C in color at the base blending into the 67-C color upper three quarters, uppermost bracts translucent, merely stained 67-C at the tips. Variegation apparent on all bracts, more so on lower bracts. Shape is acute, lanceolate with truncated base.

Floral bracts: 2 1/4×3/4 inch imbricate somewhat ovate, abruptly tipped, translucent erratically stained 67-C in color abaxial and adaxial.

Asexual reproduction:

*Method.*—Division.

*Location.*—Vista, Calif.

Inflorescence-A branched spike

Floral buds:

*Shape.*—Flattened oval.

*Length.*—2 1/2" to 2 3/4".

*Width.*—3/4" to 1".

*Color.*—151-B.

Flowers:

Barely open at anthesis.

*Size.*—Medium large; broadly bipinnate, 9"–10" by 6"–8".

*Corolla.*—Cylindrical.

*Sepals.*—1 1/2×7/16 inches, translucent, 151-B in color, three in number.

*Petals.*—2×3/8 inches 155-D in color joined 1 1/2" from base, three in number.

Fruit seed: None produced.

Reproductive organs: Typical for the genus and species.

*Ovaries.*—Superior, three locules 1/2" long by 1/4" wide, 150-D in color.

*Pistils.*—1 present.

*Style.*—2" long by 1/4" wide, 150-D in color.

*Stamens.*—6 present.

*Filament.*—1 1/2" long.

*Anthers.*—3/16" long, 7-D in color. Pollen not produced.

Disease and pest resistance: This variety has resistance to plant diseases and pests comparable to that of other variegated Guzmania cultivars.

What is claimed is:

1. A new and distinct variety of Guzmania plant named 'GUZ 224' as illustrated and described characterized by a compact arrangement of bracts, a rich red-purple coloration of floral bracts and longitudinally variegated leaves, substantially as shown and described.

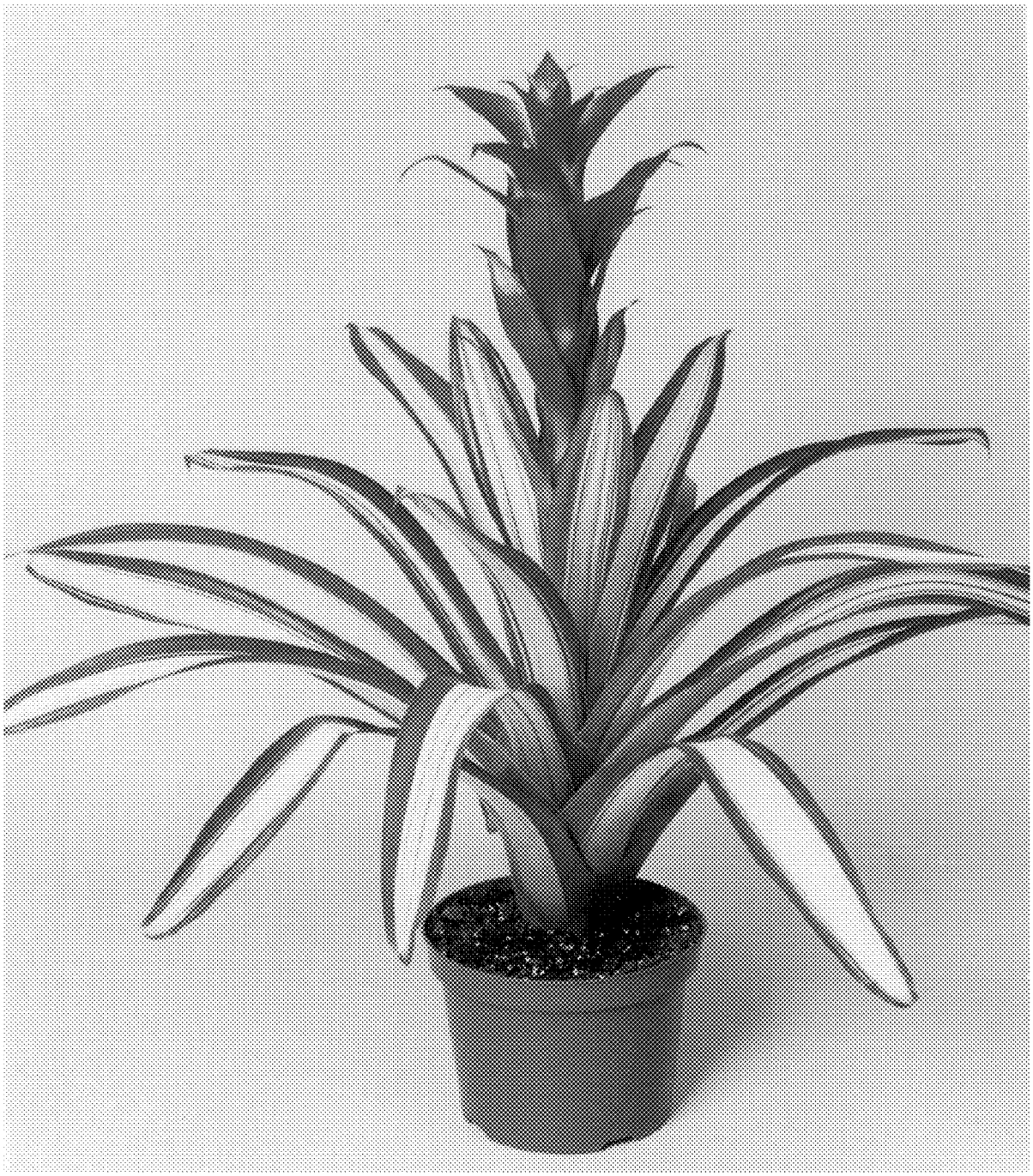

* * * * *